US008628508B2

(12) United States Patent
Weitzel et al.

(10) Patent No.: US 8,628,508 B2
(45) Date of Patent: Jan. 14, 2014

(54) MULTIDOSE VIAL ASSEMBLIES AND ADAPTERS THEREFOR

(75) Inventors: Dietmar Weitzel, Marburg (DE); Astrid Hoffmann, Marburg (DE)

(73) Assignee: Novartis AG, Basel (CH)

( * ) Notice: Subject to any disclaimer, the term of this patent is extended or adjusted under 35 U.S.C. 154(b) by 631 days.

(21) Appl. No.: 12/532,540

(22) PCT Filed: Mar. 26, 2008

(86) PCT No.: PCT/IB2008/001666

§ 371 (c)(1),
(2), (4) Date: Sep. 22, 2009

(87) PCT Pub. No.: WO2008/117178

PCT Pub. Date: Oct. 2, 2008

(65) Prior Publication Data

US 2010/0114058 A1 May 6, 2010

(30) Foreign Application Priority Data

Mar. 26, 2007 (GB) .................................. 0705782.1

(51) Int. Cl.
*A61B 19/00* (2006.01)
*A61M 5/32* (2006.01)

(52) U.S. Cl.
USPC .......................................................... 604/414

(58) Field of Classification Search
USPC ......................................... 604/403, 411, 414
See application file for complete search history.

(56) References Cited

U.S. PATENT DOCUMENTS

| | | | | |
|---|---|---|---|---|
| 5,088,996 | A * | 2/1992 | Kopfer et al. | 604/415 |
| 6,190,362 | B1 * | 2/2001 | Balestracci | 604/218 |
| 2006/0025747 | A1 * | 2/2006 | Sullivan et al. | 604/411 |
| 2006/0108319 | A1 * | 5/2006 | Meittunen | 215/386 |
| 2007/0032775 | A1 * | 2/2007 | Niedospial et al. | 604/415 |

FOREIGN PATENT DOCUMENTS

| | | | | |
|---|---|---|---|---|
| EP | 0 692 235 | | 1/1996 | |
| EP | 692235 | A1 * | 1/1996 | A61J 1/00 |
| EP | 0 909 584 | | 4/1999 | |
| EP | 1 205 173 | | 5/2002 | |
| EP | 1205173 | A2 * | 5/2002 | A61J 1/00 |
| WO | WO 98/32411 | | 7/1998 | |
| WO | WO 2005/105014 | | 11/2005 | |
| WO | WO 2005105014 | A2 * | 11/2005 | A61J 1/00 |

OTHER PUBLICATIONS

International Search Report for PCT/IB2008/001666 dated Nov. 21, 2008.

* cited by examiner

*Primary Examiner* — Melanie Hand
(74) *Attorney, Agent, or Firm* — Regina Bautista

(57) ABSTRACT

A multidose vial assembly which comprises a multidose vial (10), a withdrawal spike (30), and an adapter (60) that couples the multidose vial and the withdrawal spike together in a safe and secure manner.

32 Claims, 6 Drawing Sheets

FIG. 6
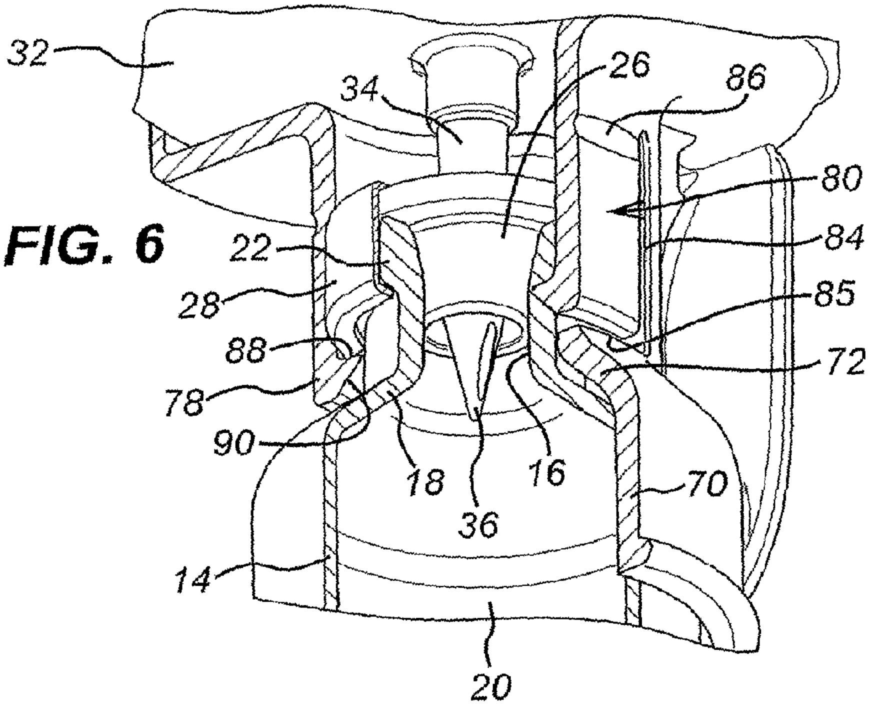
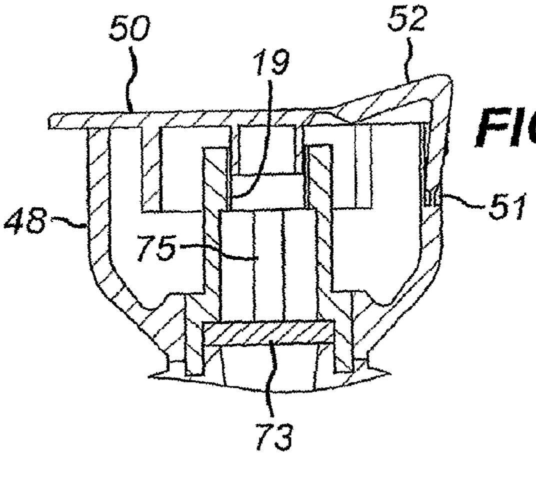
FIG. 7
FIG. 9
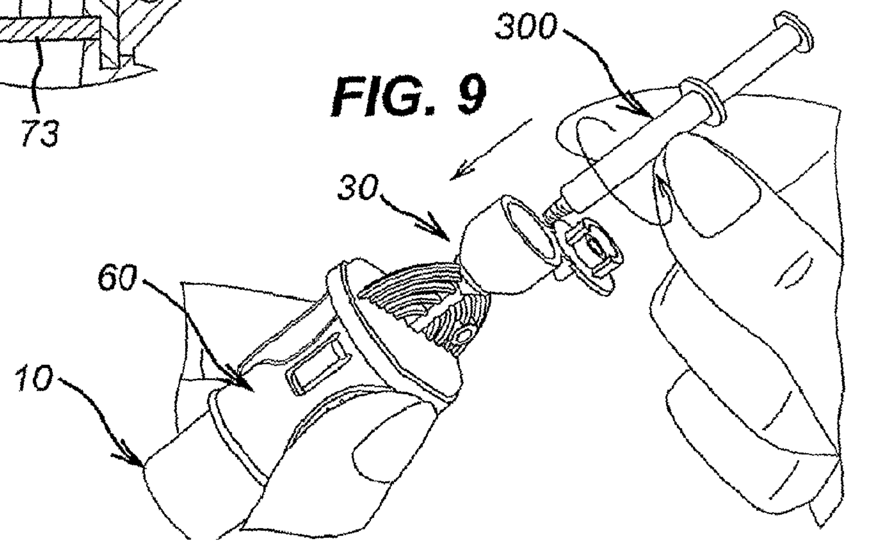

MULTIDOSE VIAL ASSEMBLIES AND ADAPTERS THEREFOR

TECHNICAL FIELD

This invention relates to multidose vial assemblies and adapters therefor. In particular, the invention concerns assemblies comprising a multidose vial, a withdrawal spike and an adapter that couples those two components together in a safe and secure manner.

BACKGROUND ART

In a standard vaccination programme, single dose vials containing substantially a single dose (e.g. 0.5 ml volume) of a given vaccine are used. Each vial is hermetically sealed on production, for example by a rubber stopper or septum which is inserted into an opening in the vial. The contents of the vial are accessed when required by puncturing the seal with a sterile injection device, such as a syringe, and withdrawing the contents into the injection device. In this manner, the contents remain sterile up to the point of injection into a subject. It is also known to use pre-filled syringes instead of single dose vials and associated injection devices.

The above approach is appropriate in most circumstances. However, where a rapid outbreak occurs (e.g. an influenza pandemic) and it is required to vaccinate a substantial proportion of a population, there might be insufficient manufacturing capacity to produce the requisite number of single dose vials. As an example, an influenza pandemic could affect millions, or even billions, of people.

This problem can be mitigated by the use of multidose vials. Vials containing more than a single dose of a drug product are known as multidose vials. Various such multidose vials are well known in the art. A typical example is illustrated in FIG. 1.

ISO 8362-1 specifies the form, dimensions and capacities of glass vials for injectable preparations. It also specifies the material from which such containers shall be made and the performance requirements of those containers. It applies to colourless or amber glass containers made from borosilicate or soda-lime glass, in the form of glass tubing, whether internally surface-treated or not, and intended for use in the packaging, storage or transportation of products intended for injection.

ISO 8362-4 specifies the shape, dimensions and capacities of glass vials for injectable preparations. It also specifies the material from which such containers shall be made and the performance requirements for the containers. It applies to colourless or amber glass containers moulded from borosilicate or soda-lime glass, with or without an internal surface treatment, and intended to be used in the packaging, storage or transportation of products intended for injection.

The multidose vial 10 comprises an outer shell 12 defining a main body portion 14 and a narrower neck portion 16. A tapering shoulder portion 18 connects the body and neck portions. The body, neck and shoulder portions together define an interior chamber 20 for containing multiple doses of a drug product. The chamber 20 might have a volume of about 6 ml, hence being sufficient to contain ten standard 0.5 ml doses of a vaccine (allowing for a standard 10% overfill allowance).

As best illustrated in FIG. 6, the neck portion 16 includes a lip 22 and defines an opening into the chamber 20. A cap 24 includes a plug portion 26, typically of rubber, that fills at least a portion of the interior space defined by the neck portion 16. The cap further includes a skirt 28, typically of aluminium, that enshrouds the lip 22. The cap 24 hence hermetically seals the opening. A flip-off disc (not shown), typically of a plastic material, overlies the upper surface of the cap 24, hence preventing contamination of the plug portion 26 prior to use.

ISO 8632-2 specifies the design, dimensions, material, performance, requirements and tests for single-use closures for injection vials covered by ISO 8362-1 and ISO 8362-4.

ISO 8632-3, ISO 8632-6 and ISO 8632-7 respectively specify details for aluminium caps for injection vials, caps made of aluminium-plastics combinations for injection vials, and injection caps made of aluminium-plastics combinations without overlapping plastics part.

It will be appreciated, however, that the multidose vial may take any suitable shape, and that the opening may be sealed in any suitable manner.

A problem associated with multidose vials is that once the seal has been penetrated in order to withdraw a first dose from the vial, the chamber may no longer be sterile. For example, penetrating a seal with an injection device could leave a puncture hole in the seal. Alternatively, where a self-sealing type of seal, such as a septum, is used, fragmentation problems might occur. An example of such fragmentation problems includes the dislodgement of a fragment of the septum into the chamber on insertion of the injection device.

Sterility may be maintained by the use of a component within the vial contents which may include preservatives such as thiomersal or 2-phenoxyethanol. It is preferred, however, that vaccines should be substantially free from mercurial material.

An objective of the invention is to maintain sterility in a multidose vial during and after the withdrawal of a first dose therefrom, without the use of preservatives within the vial contents.

Sterility may also be maintained by the use of a sterile withdrawal spike. Such sterile withdrawal spikes are known in the art. One example is the Mini Spike™ produced by B. Braun™. A typical example is illustrated in FIG. 2 and disclosed in U.S. 2002/0040206 (the contents of which is hereby incorporated by reference). The sterile spike 30 comprises a housing 32 and a piercing thorn 34 protruding centrally and perpendicularly from the housing. The housing 32 is plate-shaped and comprises a first filter chamber 3 containing a fluid filter 5 and a second filter chamber 7 containing an air filter 9 (see FIG. 8). The thorn 34 has a piercing tip 36. A fluid duct 11 and an air duct 13 extend in longitudinal direction through the piercing thorn 34. Said two ducts end in the conical area of the tip 36 of the piercing thorn 34. Inside the housing 32 the ducts are isolated from each other. The fluid duct 11 communicates with the fluid filter chamber 3, and the air duct 13 communicates with the air filter chamber 7. The fluid filter chamber 3 is further connected with a duct 15 which extends through a tube 38 which, in extension of the piercing thorn 34, is connected with the housing 32 and protrudes to the opposite side of the housing 32. Two wing-shaped portions 40, 42 laterally engage with the tube 38, said wing-shaped portions 40, 42 being configured as quadrantal sectors and extending between the tube 38 and the housing 32. The two wing-shaped portions 40, 42 together form a semicircle located in a plane extending at right angles to the plane of the plate-shaped housing 32. On both sides of the wing-shaped portions 40, 42 concentric ribs 44 are provided which facilitate the gripping by hand. Thus the wing-shaped portions 40, 42 form a gripping part, and the plate-shaped housing 32 forms a manually actuated impact surface when the piercing thorn 34 is inserted into a stopper, such as the cap 24 of the multidose vial 10.

In the wing-shaped portion 40 a vent hole 46 communicating with the air filter chamber 7 is provided. In the air flow path the air filter membrane 9 contained in the air filter chamber 7 is arranged between the air duct 13 and the vent hole 46. It is envisaged that a withdrawal spike for use in the present invention could omit the fluid filter membrane 9, since this could conceivably inhibit flow of component out of the vial.

At the end of the tube 38 a connecting piece 17 having an inner cone 19 and externally threaded ribs 21 of a Luer-Lock connector is arranged (see FIG. 8). Said connecting piece 17 is annularly surrounded, at a lateral distance, by a protective jacket 48. Said protective jacket 48 comprises a bottom portion 49 sealingly adjoining the base part of the connecting piece 17. The protective jacket 48 protrudes beyond the outer end of the connecting piece 17. At the edge of the pot-shaped protective jacket 48 a hinged cover 50 is fastened by a living hinge 51. Said cover 50 is further connected via a toggle joint arm 52 with the protective jacket 48. Said toggle joint arm 52 effects a snapping behaviour of the cover 50 which assumes either an open position (FIG. 8) or a closed position (FIGS. 1, 4, 5 and 7). On the inside of the cover a projecting edge 53 is arranged which, in the closed position of the cover 50, fittingly engages with the protective jacket 48. Further, a cylindrical closing part 54 (FIG. 8) is provided on the inside of the cover 50, said closing part 54 entering the inner cone of the connecting piece 17 in the closed position.

Inside the connecting piece 17 a valve 71 is arranged (see FIG. 8 in particular). Said valve 71 comprises a valve disk 73 and a valve opener 75. The edge of said valve disk 73 of elastomeric material is clamped between the edge of the tube 38 and an edge of the connecting piece 17 and is gripped over by a sleeve 23 of the connecting piece. The valve disk 73 comprises a slot or opening structure. It is of the self-closing type, i.e. without exertion of external pressure it assumes the closed position shown in the drawings.

The valve opener 75 is a tubular part containing a longitudinal duct 77 having an end pushing against the central portion of the valve disk 73. On the circumferential area of the valve opener 75, projections (not shown) protruding to the outside are arranged which are distributed over the circumference. The upper ends of said projections push against an annular shoulder 25 inside the connecting piece 17. Above the annular shoulder 25 the inner cone 19 is located.

Below the valve disk 73 a cavity 79, which is enlarged relative to the duct through the tube 38, is provided and the valve disk can move into said cavity 79 when it is deformed by the valve opener 75.

During use of the withdrawal spike 30 a male Luer cone is placed upon the connecting piece 17, or the cone 302 of a syringe 300 is inserted into the inner cone 19. During this process the penetrating part pushes against the front face of the valve opener 75 whereby the latter is displaced inside the connecting piece 17 thus pressing the valve disk 73 open. The valve 71 is thus forced to remain in the open position as long as the external part protrudes into the connecting piece 17. Thereafter the spring action of the valve disk 73 causes valve opener 75 to return into its initial position, and the valve 71 closes again.

Any fluid residues in the connecting piece 17 or in the valve 71 are prevented from flowing out by closing the cover 50.

It will be appreciated that the above description of the sterile withdrawal spike is purely by way of example, and that any suitable sterile withdrawal spike may be used in conjunction with the invention. In particular, it is possible to omit the internal valve 71.

A drawback of inserting such a withdrawal spike 30 into a multidose vial 10 is that the spike 30 is not secured to the vial 10 other than by frictional forces between the thorn 34 and the cap 24. The spike 30 is therefore liable to be displaced from and within the vial 10. Possible displacements include: an axial displacement, wherein the thorn 34 is displaced axially relative to the cap 24; and/or an orientational displacement (or a wobble), wherein the longitudinal axis of the thorn 34 becomes non-parallel with a longitudinal axis of the vial 10. This has potentially serious consequences. In a worst case, the spike may be displaced to such an extent that the thorn 34 is completely dislodged from the puncture hole that it has created in the cap 24. The vial 10 would then have to be discarded without further use, i.e. wasting any remaining doses, because of the risk of lack of sterility due to the exposed puncture hole and/or to the need to insert another withdrawal spike 30.

Even if the thorn 34 were not completely dislodged, any displacement thereof from an ideal predetermined position within the vial 10 could have serious consequences. The ideal position of the thorn 34 with respect to the vial 10 locates the thorn tip 36 at a predetermined depth within the vial chamber 20. The predetermined depth is selected so that the thorn tip 36 is inserted beyond the cap 24 so that the two ducts in the conical area of the tip 36 are not blocked at all by the cap 24, which could hinder withdrawal of the vial contents.

Another consideration is to minimise wastage of the vial contents. Typically, the vial contents are withdrawn by inverting the assembled vial 10 and spike 30 so that gravity urges the contents towards the vial cap 24, whence the contents can be withdrawn via the thorn 34, specifically via the fluid duct thereof and its opening in the thorn tip 36. With the assembly inverted, any contents lying between the cap 24 and the fluid duct opening in the thorn tip 36 are inaccessible and hence cannot be withdrawn. Accordingly, if the thorn tip 36 were to be inserted beyond the depth necessary for its ducts to be clear of the cap 24, then the volume of inaccessible contents would increase.

Yet another consideration is to ensure central penetration of the cap 24 by the piercing tip 36 of the thorn 34. If the penetration were to be significantly off-centre, there is a risk that the duct openings in the tip 36 could become at least partially blocked by the interior wall of the vial neck portion 16.

It is therefore desirable to ensure that the spike 34 is inserted to the correct predetermined depth within the vial 10, and at the right location and orientation. This might be accomplished by skilful manipulation by a user. For example, a skilled practitioner might be able to insert the spike 34 to the correct depth and at the right location and orientation. However, this approach is liable to human error and a consistent insertion could not be ensured.

It is also desirable to secure the spike 30 to the vial 10 to eliminate the displacement issues noted above. Again, this might be accomplished by a skilled practitioner who might be able to hold the spike 30 to the vial 10 to prevent their relative displacement. However, this approach is again liable to human error and further might require the use of both hands and/or awkward manipulation. A more user-friendly, less fatiguing approach is therefore desirable.

An ancillary problem associated with known withdrawal spikes 30 such as that described above relates to the valve 71 within. With the valves that are typically used, it is possible for fluid residues to become trapped in the valve, where bacteria could collect and hence pose a contamination risk to subsequent fluid withdrawals through the spike 30. In particular, fluid residues may be trapped in difficult to access areas within the valve, particularly in the area above the valve disk 73, such as in the recess between the inner cone 19 and the top of the valve opener 75.

Swabbable valves, which present a flush upper surface when in a sealed, closed position for easy swabbing, e.g. by disinfectant, are known. One known manufacturer of such valves is Halkey-Roberts.

It is therefore envisaged that spikes 30 for use in connection with this invention could be provided with such a swabbable valve. In particular, a swabbable valve could be housed within the connecting piece 17 so as to present an upper surface that, when in the closed position, is flush with the upper surface of the connecting piece. With such an arrangement, the problematic recess between the inner cone 19 and the top of the valve opener 75 would be removed. Indeed, it is envisaged that withdrawal spikes could, in general and independently of any association with an adapter, be provided with swabbable valves to benefit from the advantages associated therewith of eliminating areas within which bacteria can collect.

As indicated above, one possible application of the invention is for a pandemic influenza vaccination programme. Influenza vaccines are described in more detail in chapters 17 & 18 of *Vaccines*. (eds. Plotkin & Orenstein). 4th edition, 2004, ISBN: 0-7216-9688-0.

It is an object of the invention to provide further and improved methods and devices for delivering vaccines, and in particular to increase the safety thereof.

DISCLOSURE OF THE INVENTION

The invention facilitates the coupling of a withdrawal spike with a multidose vial in a safe and secure manner.

According to a first aspect, the invention provides an adapter configured to couple a withdrawal spike with a vial, the adapter comprising:

- a hollow body defined by an outer wall having a first end and a second end;
- a first retaining member at the first end adapted to retain at least a portion of the vial; and
- a second retaining member at the second end adapted to retain at least a portion of the withdrawal spike,
- such that the withdrawal spike is locatable in a predetermined position with respect to the vial.

According to a second aspect, the invention provides an assembly comprising:

- a vial;
- a withdrawal spike; and
- an adapter, the adapter comprising:
  - a hollow body defined by an outer wall having a first end and a second end;
  - a first retaining member at the first end retaining at least a portion of the vial; and
  - a second retaining member at the second end retaining at least a portion of the withdrawal spike,
- such that the withdrawal spike is located in a predetermined position with respect to the vial.

According to a third aspect, the invention provides a method of assembling an assembly for administering multiple doses of a component, comprising the steps of:

- providing a vial containing the component;
- providing a withdrawal spike;
- providing an adapter in accordance with the first aspect of the invention;
- fitting the adapter onto the vial; and
- fitting the withdrawal spike onto the adapter.

According to a fourth aspect, the invention provides a method of preparing multiple doses of a component comprising the steps of:

- assembling the assembly in accordance with the third aspect of the invention;
- inserting an injection device into the withdrawal spike;
- withdrawing substantially a dose of component from the vial into the injection device through the spike; and
- repeating the inserting and withdrawal steps using further injection devices.

As described above, the vial will generally be a multidose vial, preferably without preservatives.

The Adapter

The first retaining member may comprise at least one inwardly extending first projection. The or each first projection may be disposed at a free end of an associated resiliently deflectable tab that is defined by a pair of slots in the outer wall, the slots extending at least partially from the first end towards the second end of the outer wall. The or each first projection may include a camming surface for engagement by at least a portion of the multidose vial. The outer wall may include a thinned portion between the ends of the pair of slots at the fixed end of the or each tab to aid tab deflection.

The adapter may further comprise a flange extending from the second end. In this case, the second retaining member may comprise at least one inwardly extending second projection disposed on the outer periphery of the flange. The or each second projection may be disposed at a free end of an associated resiliently deflectable tab that has a fixed end at the outer periphery of the flange. The or each second projection may include a camming surface for engagement by at least a portion of the withdrawal spike. Optionally, the or each tab includes a thinned portion at the fixed end to aid tab deflection.

Where the adapter includes a flange extending from the second end, the flange may comprise an annular disc that includes a rim extending about at least a portion of the flange periphery, the flange and rim configured to receive a housing of the withdrawal spike.

The adapter may further comprise a skirt projecting from the first end of the body. The skirt may be configured to enshroud at least a portion of the vial, with an inner surface of the skirt having a shape that is adapted to match the contours of the relevant portion of the vial.

The adapter may further comprise at least one gripping surface. This may comprise a pair of opposed gripping surfaces, each disposed on an outer surface of a boss projecting outwardly from the outer wall of the body.

The adapter may comprise a unitary piece. The adapter may comprise a thermoplastic moulding.

In accordance with the second aspect of the invention, the vial may comprise a shell defining an interior chamber having an opening and a cap hermetically sealing the opening. The chamber may contain multiple doses of a vaccine, such as an influenza vaccine. The cap may be received in the hollow body of the adapter and may be engaged by the first retaining member. The cap may comprise a septum or a swabbable valve.

The withdrawal spike may comprise a housing and a piercing thorn, the thorn protruding centrally and perpendicularly from the housing. The predetermined position may comprise the thorn of the withdrawal spike being inserted through the vial cap by a predetermined distance. The spike housing may be received in the adapter flange and may be engaged by the second retaining member.

In accordance with the third aspect of the invention, where the vial comprises a shell defining an interior chamber having an opening and a cap hermetically sealing the opening, and where the or each first projection includes a camming surface for engagement by at least a portion of the vial, the step of fitting the adapter onto the vial may comprise: engaging the camming surface of the or each first projection with the vial cap; resiliently deflecting outwardly the associated deflectable tab to a deflected position via a relative axial force between the vial and the adapter; and passing the cap beyond the or each first projection, the or each first projection hence returning from the deflected position to retain the cap within the hollow body.

Alternatively or additionally, in accordance with the third aspect of the invention, where the withdrawal spike comprises a housing and a piercing thorn, the thorn protruding centrally and perpendicularly from the housing, and where the or each second projection includes a camming surface for engagement by at least a portion of the withdrawal spike, the step of fitting the withdrawal spike onto the adapter may comprise: engaging the camming surface of the or each second projection with the spike housing; resiliently deflecting outwardly the associated deflectable tab to a deflected position via a relative axial force between the spike and the adapter; and passing the housing beyond the or each second projection, the or each second projection hence returning from the deflected position to retain the spike housing against the adapter flange.

In accordance with either the third or the fourth aspect of the invention, the component may comprise a vaccine, such as an influenza vaccine.

A vial will typically be made of a glass or plastic material. Where a glass is used, then it is preferred to use a borosilicate glass rather than a soda lime glass.

A vial is preferably sterilized before a component is added to it.

To avoid problems with latex-sensitive patients, the devices preferably do not include latex components.

An assembly according to the second aspect of the invention may be packaged together with a delivery device, such as a syringe, or may be packaged together with a set of such delivery devices corresponding to the number of doses contained in the vial. Where a composition/component is packaged with a syringe, the syringe will not normally have a needle attached to it, although a separate needle may be supplied with the syringe for assembly and use. Thus, delivery devices do not necessarily come packaged with an associated needle unit, but are suitable to have a needle unit attached to them.

Methods of Treatment, and Administration of the Vaccine

Devices of the invention are suitable for administration of vaccines to human or animal patients, and the invention provides a method of raising an immune response in a patient, comprising the step of administering a composition from a vial to the patient.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

BRIEF DESCRIPTION OF DRAWINGS

The invention is described, purely by way of example, by reference to the attached Figures, in which:

FIG. 6 illustrates a detail, partial cut-away perspective view of the assembly of FIG. 5;

FIG. 7 illustrates a detail, cut-away view of the upper portion of the withdrawal spike component of the invention;

FIG. 9 illustrates a schematic step of connecting a syringe to an assembly of the invention.

MODES FOR CARRYING OUT THE INVENTION

Adapter

Figure 1:
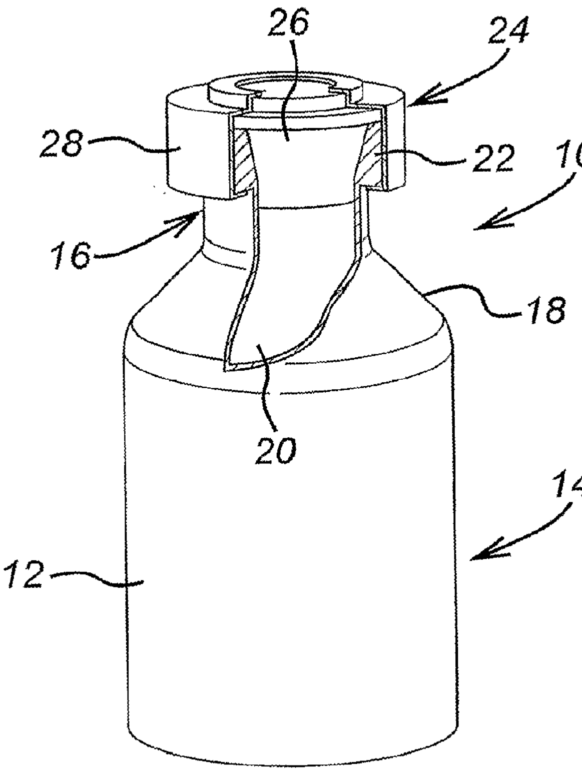
FIG. 1 illustrates, in a cut-away perspective view, a known vial.

An adapter 60 comprises a hollow cylindrical body 62 defined by an outer wall 63 having a first end 64 and a second end 66 and a longitudinal axis. A skirt 68 projects from the first end 64 of the body 62. The skirt 68 includes a substantially cylindrical body 70 having the same longitudinal axis but a greater diameter than the body 62. A tapered shoulder portion 72 connects the skirt body 70 to the adapter body 62. A circular flange 74 extends outwardly from the second end 66 of the outer wall 63. The flange 74 extends in a plane that is perpendicular to the longitudinal axis of the body 62. At the periphery of the flange 74, there is disposed a diametrically opposed pair of upstanding rim portions 76.

A first retaining member is provided at the first end of the adapter body 62 for securely retaining a multidose vial 10. The multidose vial 10 may be of the known type discussed in the opening portion of the specification with reference to FIGS. 1 and 6. The first retaining member comprises a diametrically opposed pair of inwardly extending first projections 78, each disposed at a free end 80 of an associated resiliently deflectable tab 82. Each tab 82 is defined by a pair of parallel, axial slots 84 in the outer wall 63, the slots 84 extending at least partially from the first end 64 towards the second end 66 of the outer wall, and a perpendicular slot 85 interconnecting the slots 84 at the first end 64. At the fixed end of each tab 82, a dimple 86 is formed in the outer wall 63 to provide a portion of reduced thickness for a purpose to be described below. Each first projection 78 includes a flat portion 88 extending in a plane perpendicular to the longitudinal axis of the adapter body 62 and an oblique camming surface 90 that together define a wedge shaped profile, being thinner at the first end 64 of the adapter body 62 than towards the second end 66 thereof.

A second retaining member is provided at the second end 66 of the adapter body 62 for securely retaining a withdrawal spike 30. The withdrawal spike 30 may be of the known type discussed in the opening portion of the specification with reference to FIG. 2. The second retaining member comprises a diametrically opposed pair of inwardly extending second projections 92, each disposed at a free end 94 of an associated resiliently deflectable tab 96. Each tab 96 has a fixed end at the outer periphery of the flange 74. At the fixed end of each tab 96, a dimple 98 is formed to provide a portion of reduced thickness for a purpose to be described below. Each second projection 92 includes a flat portion 100 extending in a plane parallel to the plane of the flange 74 and an oblique camming surface 102 that together define a wedge shaped profile, being thinner at the free end 94 of the tab 96 than towards the fixed end thereof.

The pair of second projections 92 is disposed perpendicularly to the pair of first projections 78. That is to say, the first projections 78 are arranged at 0° and 180° about the adapter circumference, whilst the second projections 92 are arranged at 90° and 270° respectively.

The adapter 60 further includes a diametrically opposed pair of gripping surfaces 104. Each gripping surface is disposed on an outer surface of a boss 106 projecting from the outer wall 63. The gripping surfaces are arranged in line with the second projections 92, i.e. at 90° and 270° about the adapter circumference respectively. The gripping surfaces are ergonomically contoured to be gripped between a user's finger and thumb.

The adapter 60 comprises a unitary piece. That is to say, the body 62, skirt 68 and flange 74, and all components thereof are integrally formed. The adapter may suitably be formed by moulding. The adapter may be moulded from a thermoplastic material.

Assembly

The outer wall 63 of the adapter 60 has an interior surface that is sized and shaped to receive the cap 24 of the multidose vial 10, i.e. the interior surface has a diameter that substantially matches the outer diameter of the cap skirt 28. The close fit of the cap 24 within the adapter body 62 ensures that the adapter 60 is centrally and firmly secured to the multidose vial 10 with minimal axial misalignment of the adapter 60 and vial 10.

The first retaining member engages the cap 24. In particular, the flat portions 88 of the first projections 78 engage the underside of the cap skirt 28. The interengagement prevents the vial 10 from being displaced axially out of the adapter 60. Preferably, the interengagement is irreversible such that once the adapter 60 has been retained on the vial cap 24 it is locked in place. This locking will not only prevent accidental relative displacement of the vial 10 and the adapter 60, but will also prevent deliberate attempts to remove the adapter 60 from the vial 10.

The adapter skirt body 70 and shoulder portion 72 together define an interior surface that is sized and shaped to receive an upper portion of the multidose vial 10 including at least part of the vial body portion 14 and the vial shoulder portion 18. In particular, the adapter skirt interior surface has a profile that substantially matches that of the relevant portion of the outer surface of the outer wall 63. The close fit of the upper portion of the vial 10 within the adapter skirt 68 further ensures that the adapter 60 is centrally and firmly secured to the vial 10 with minimal axial misalignment of the adapter 60 and vial 10. In addition, excessive axial displacement of the vial 10 into the adapter body 62 is prevented by the interengagement of the respective adapter skirt and vial shoulder portions 72, 18.

The flange 74 and rim portions 76 are sized and shaped to receive the plate-shaped housing 32 of the withdrawal spike 30, i.e. the inner diameter of the rim portions 76 substantially matches the outer diameter of the spike housing 32. The close fit of the spike housing 32 on the adapter flange 74 and within the rim portions 76 ensures that the withdrawal spike 30 is centrally received within the adapter 60. Since the flange 74 has a planar surface that is perpendicular to the adapter longitudinal axis and since the spike thorn 34 protrudes perpendicularly from the disc-shaped spike housing 32, when the spike housing 32 is received on the flange 74 the longitudinal axis of the spike thorn 34 is coincident with that of the adapter 60.

By virtue of the central, axially aligned connection of the adapter 60 to the vial 10, and by virtue of the central, axially aligned connection of the withdrawal spike 30 to the adapter 60, the spike thorn 34, is centrally and axially aligned with the vial 10.

The second retaining member engages the withdrawal spike 30. In particular, the flat portions 100 of the second projections 92 engage the upper surface of the spike housing 32. The interengagement prevents the spike 30 from being displaced axially out of the adapter 60. Preferably, the interengagement is irreversible such that once the spike 30 has been retained on the adapter 60 it is locked in place. This locking will not only prevent accidental relative displacement of the spike 30 and the adapter 60, but will also prevent deliberate attempts to 10 remove the spike 30 from the adapter 60.

The adapter 60 thus serves as an intermediary member to couple the withdrawal spike 30 with the multidose vial 10. The adapter locates the withdrawal spike 30 is in a predetermined position with respect to the multidose vial 10 when the withdrawal spike 30 is coupled to the multidose vial 10 by the adapter 60. The predetermined position corresponds to the spike thorn 34 being in axial alignment with the longitudinal axis of the multidose vial 10 and at a depth just sufficient to ensure that the duct openings of the thorn tip 36 are not blocked by the plug 26 of the cap 24 and yet not so deep as to include a significant volume between the underside of the plug 26 and the fluid duct opening in the thorn tip 36.

Method of Assembling

The multidose vial 10 and the withdrawal spike 30 are coupled via the adapter 60 in the following manner.

First, the withdrawal spike 30 is fitted to the adapter 60. In particular, the spike housing 32 is inserted onto the adapter flange 74 by relative axial motion between the withdrawal spike 30 and the adapter 60. On further relative axial motion, the underside of the spike housing 32 is brought into contact with the second projections 92. By virtue of the oblique angle of the camming surfaces 102, urging the spike 30 axially relative to the adapter 60 urges the second projections 92 to be deflected radially outwardly via resilient deflection of the free ends 94 of the tabs 96 from which the second projections 92 extend. The dimples 98 aid the deflection of the tabs 96. The radial deflection continues until the second projections 92 are sufficiently deflected to allow the passage of the spike housing 32, i.e. until the deflected second projections 92 define an inner diameter that is equal to the outer diameter of the spike housing 32. The spike housing 32 is then passed through the second projections 92 until the underside of the spike housing 32 has passed beyond the second projections 92. At that point, the tabs 96 are urged to return from their deflected positions by virtue of their resilience, whereupon the flat portions 100 overlie the upper surface of the spike housing 32 to retain the spike housing 32 within the flange 74 and rim portions 76 as discussed above.

This first stage is typically carried out at the point of manufacture, such that a pre-assembled spike and adapter unit is typically shipped to the end user. However, it will be appreciated that this first stage may alternatively be carried out at the point of use or at any intermediate stage in the supply chain.

Second, the adapter 60 is fitted to the vial 10. This second stage is typically carried out at the point of use (i.e. by the person administering the vial contents). However, it will be appreciated that this second stage may alternatively be carried out at the point of manufacture or at any intermediate stage in the supply chain. In particular, the flip-off disc of the cap 24 has to be removed from the vial 10, the upper surface of the cap 24, particularly the plug portion 26 thereof, is swabbed with a disinfectant and then the vial 10 is inserted into the adapter skirt 68 by relative axial motion between the adapter 60 and the vial 10. In this regard, the flared shape of the skirt 68 assists in the insertion. On further relative axial motion, the upper surface of the cap 24 enters the first end 64 of the adapter body 62 and is brought into contact with the first projections 78. By virtue of the oblique angle of the camming surfaces 90, urging the vial 10 axially relative to the adapter 60 urges the first projections 78 to be deflected radially outwardly via resilient deflection of the free ends 80 of the tabs 82 from which the first projections 78 extend. The dimples 86 aid the deflection of the tabs 82. The radial deflection continues until the first projections 78 are sufficiently deflected to allow the passage of the cap 24, i.e. until the deflected first projections 78 define an inner diameter that is equal to the outer diameter of the cap 24, notably the outer diameter of the cap skirt 28. The cap 24 is then passed through the first projections 78 until the underside of the cap skirt 28 has passed beyond the first projections 78. At that point, the tabs 82 are urged to return from their deflected positions by virtue of their resilience, whereupon the flat portions 88 underlie the underside of the cap skirt 28 to retain the cap 24 within the adapter body 62 as discussed above.

Hence, typically, the withdrawal spike 30 is first connected to the adapter 60 and then the vial 10 is connected to the assembled withdrawal spike 30 and adapter 60. It will be appreciated, however, that the fitting order may be reversed, such that the adapter 60 is first connected to the vial 10 and then the spike 30 is connected to the assembled vial 10 and adapter 60. During fitting the withdrawal spike 30 to the assembled vial 10 and adapter 60 in this alternative, the piercing tip 36 of the thorn 34 is brought into contact with the upper surface of the cap 24 and subsequently penetrates and passes through the cap plug 26 until it reaches the above-mentioned predetermined position. The assembly process may either be manual or automated, or a combination of the two.

Method of Preparing Multiple Doses of a Component

The assembly can be used in the preparation of multiple doses of a component. A first dose is withdrawn from the multidose vial chamber 20 by inserting an injection device, such as a syringe, into the withdrawal spike 30 and drawing substantially a dose of, for example 0.5 ml volume, into the injection device via the spike 30 in a conventional manner. This might include inverting the assembly to ensure that the component is accessible by the fluid duct of the thorn tip 36. A second and subsequent doses are then withdrawn by inserting, in turn, subsequent injection devices into the spike 30 and correspondingly drawing substantially a dose into each subsequent injection device via the spike 30 in a conventional manner. The insertion and withdrawal steps are continued until the vial contents are depleted.

It should be noted that the correct depth of insertion of the spike thorn tip 36 that is assured by the spike and adapter assembly enables the maximum amount of contents to be removed from the multidose vial 10 to the extent that it may be possible to withdraw an additional dose over the nominal specified number of doses for the multidose vial 10, by virtue of the overfill allowance mentioned above. Thus, the invention has the potential to reduce wastage and hence to provide a more efficient administration of vial contents.

It will be appreciated that alternative devices and methods can be envisaged by combining features as appropriate from each of the foregoing examples.

The foregoing description of the invention has been provided by way of example. It will be appreciated that numerous variations in detail can be made without departing from the spirit and scope of the invention.

For example, the invention has been discussed in the context of vaccination against influenza, but it would be equally applicable to vaccination against other viruses.

Moreover, the adapter 60 has been described to be fitted to the known type of multidose vial 10 illustrated in FIG. 1, and hence has a shape and configuration appropriate to such a vial. However, it has been made clear that the invention is not limited in application to such vials 10 and accordingly the shape and configuration of the adapter 60 may be adapted *mutatis mutandis* to suit other sized and shaped multidose vials. Typically, the adapter 60 has a shape and configuration appropriate to ensure the closest possible fit to an ISO standard vial 10.

Figure 2:
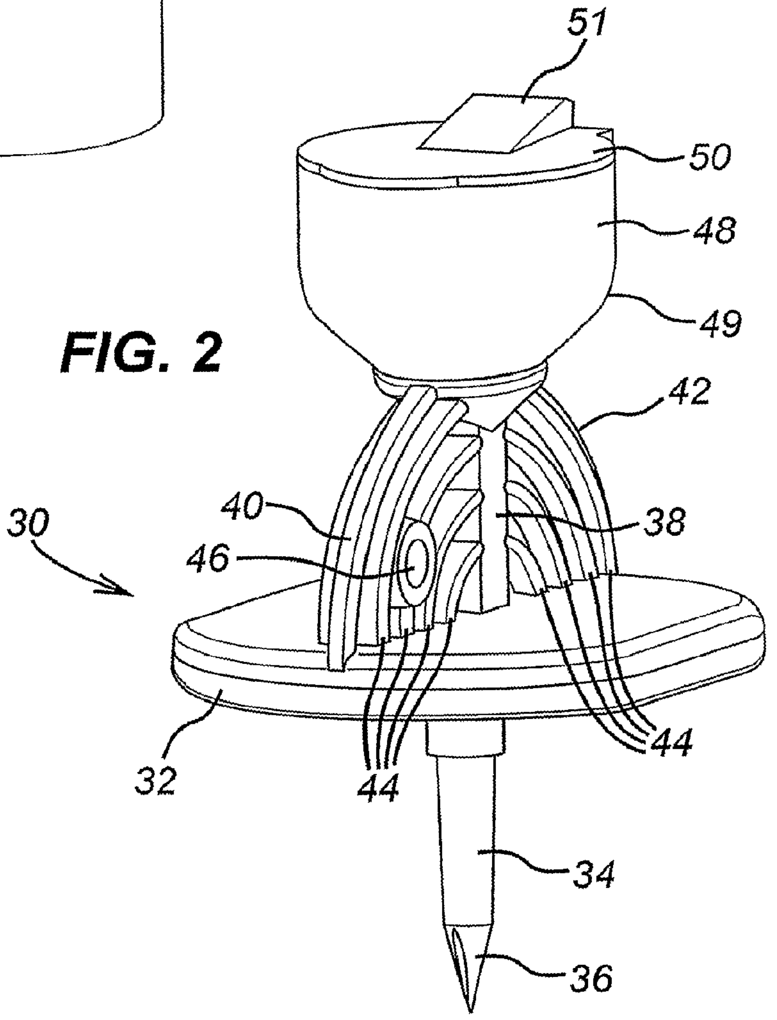
FIG. 2 illustrates, in a perspective view, a known sterile withdrawal spike.
Figure 3A:
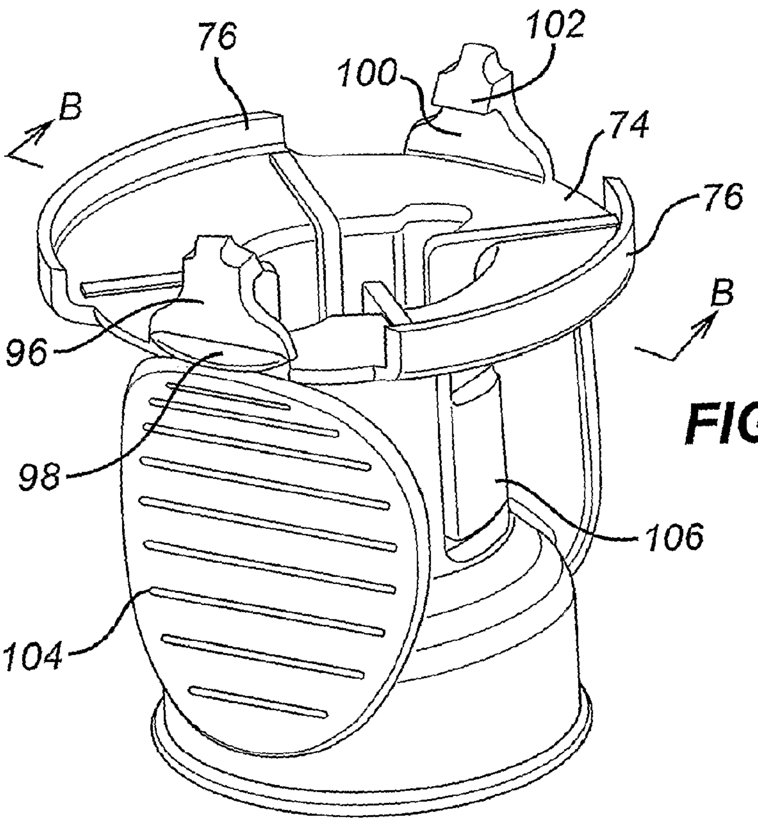
FIG. 3A illustrates, in a perspective view, an adapter of the invention.
Figure 3B:
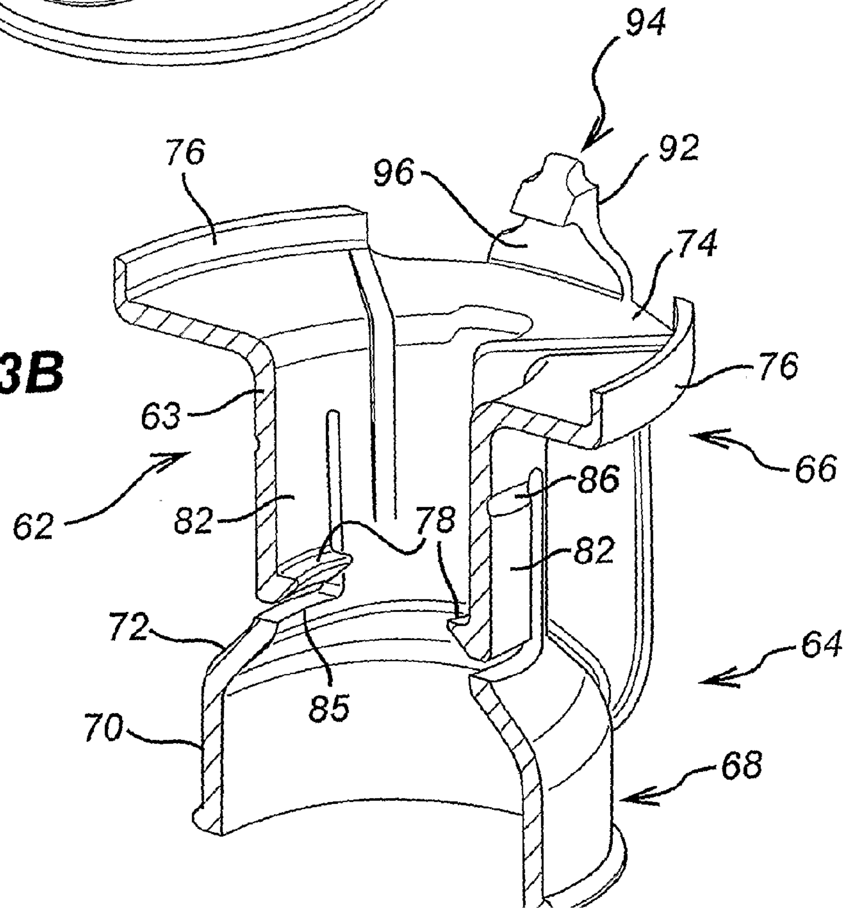
FIG. 3B illustrates, a cut-away view along line B-B of FIG. 3A.
Figure 4:
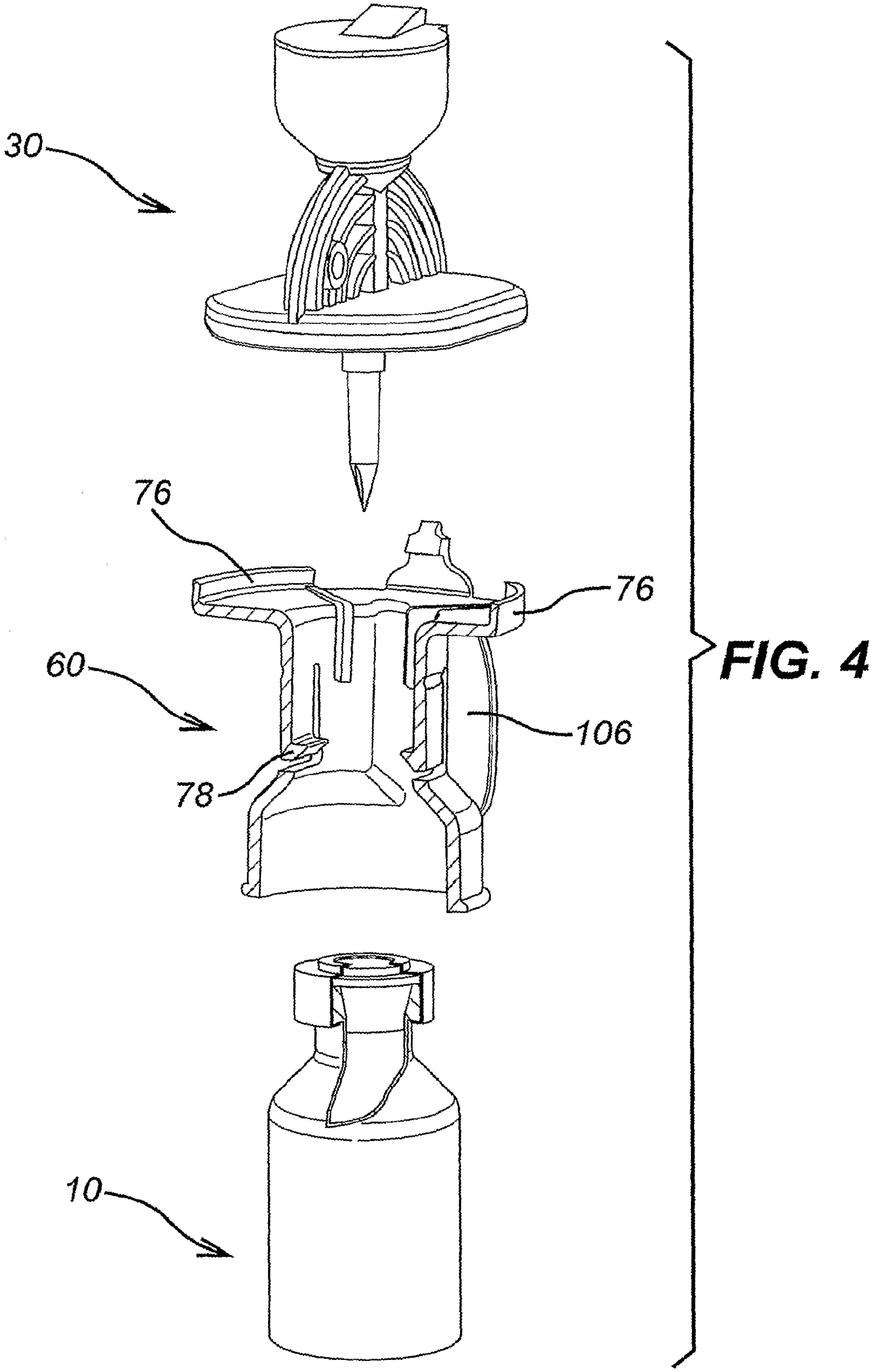
FIG. 4 illustrates an exploded view of the three components of an assembly of the invention axially aligned prior to assembly.
Figure 5:
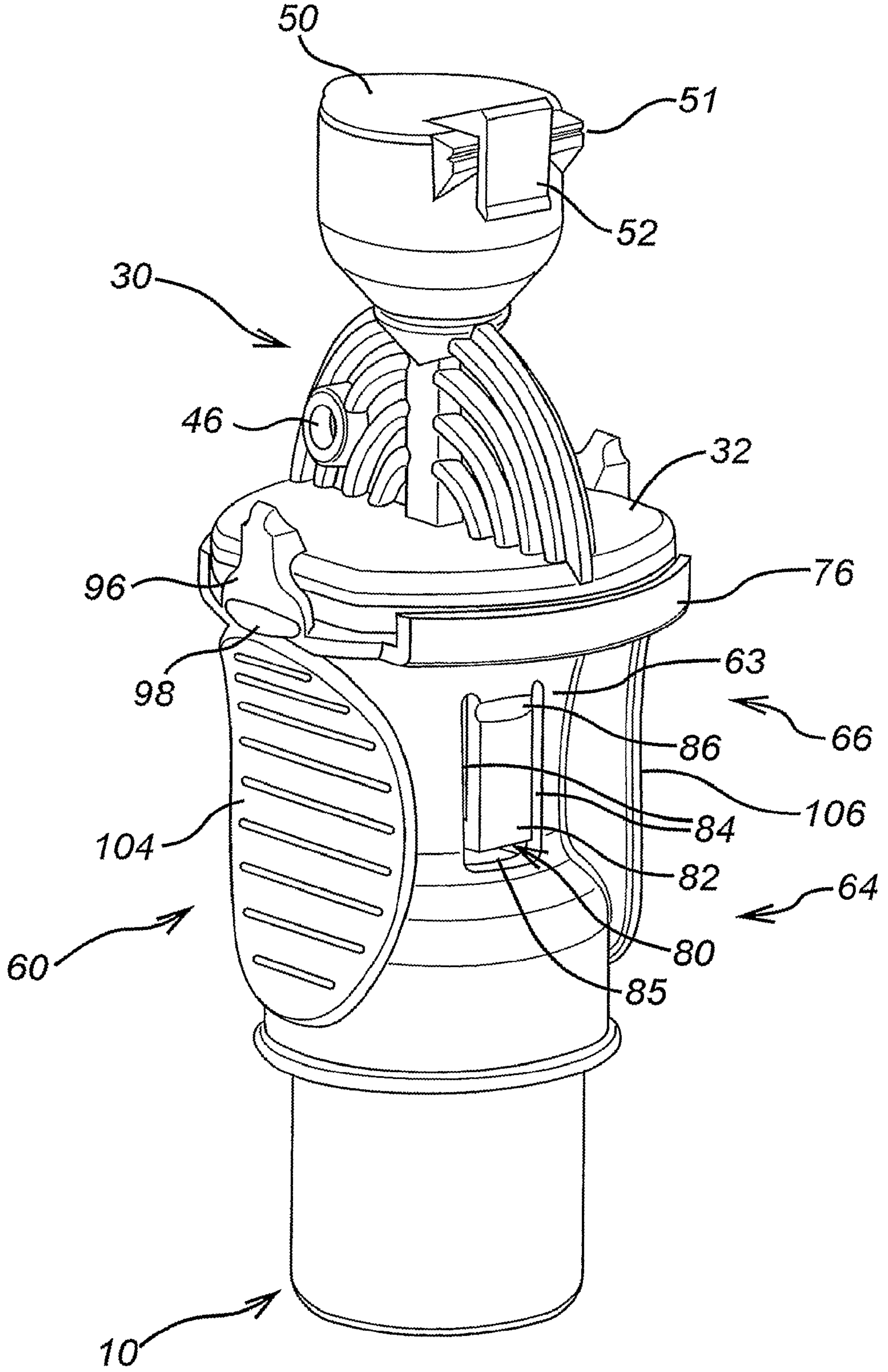
FIG. 5 illustrates an assembly of the invention in assembled form.
Figure 8:
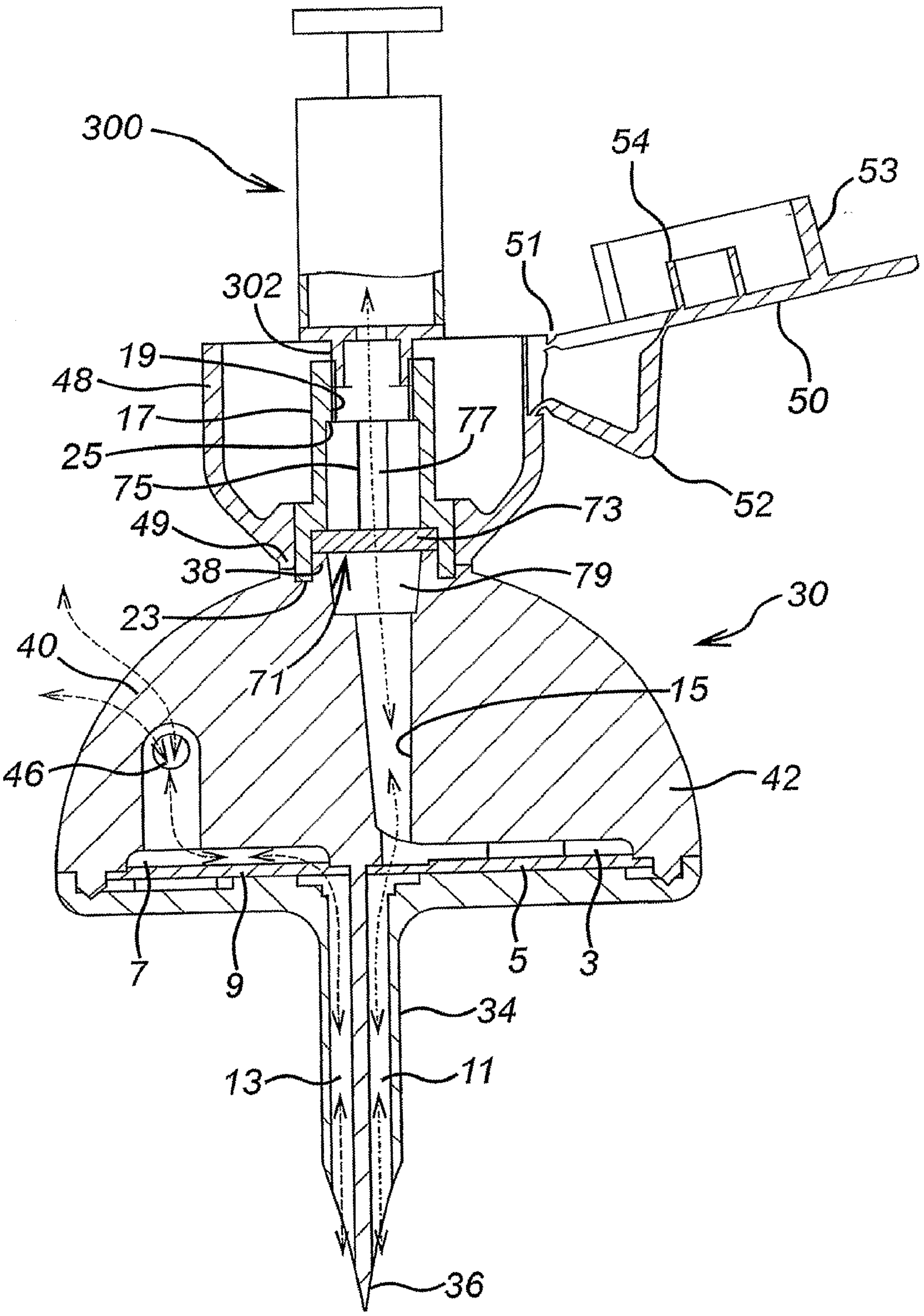
FIG. 8 illustrates, schematically and in cross-section, a syringe connected to the withdrawal spike component of the invention, the adapter and vial components being omitted for clarity.

Similarly, the adapter 60 has been described to be fitted to the known type of withdrawal spike 30 illustrated in FIG. 2, and hence has a shape and configuration appropriate to such a spike. However, it has been made clear that the invention is not limited in application to such spikes 30 and accordingly the shape and configuration of the adapter 60 may be adapted *mutatis mutandis* to suit other sized and shaped withdrawal spikes.

Moreover, it has been found that the liquid filter of standard withdrawal spikes 30, which is typically included to block bacteria from entering a vial to which the spike is attached, could interfere with the smooth withdrawal of vial contents from the vial 10. Accordingly, the liquid filter may be omitted from a withdrawal spike 30 for use with the present invention.

Although a desirable feature, the adapter skirt 68 is not necessary. If no skirt 68 were provided, excessive axial displacement of the vial 10 into the adapter 60 could be prevented by interengagement of the first end 64 of the adapter body 62 and the shoulder portion 18 of the vial.

The first and second retaining members need not comprise respective pairs of projections 78, 92. Instead, they might comprise a greater number of projections 78, 92. Alternatively, each retaining member could comprise a single projection, i.e. an annular projection. In this case, the single projection would not be disposed on a resiliently deflectable tab. Instead, the whole projection would have to be resiliently expandable.

The grip surfaces 104 need not be diametrically disposed, nor be in line with second projections 92.

In tests, where single doses were withdrawn daily from the chamber 20 of an assembled multidose vial 10, adapter 60 and withdrawal spike 30, the contents of 479 out of 480 such assemblies remained sterile after ten doses had been withdrawn. The doses were withdrawn according to good clinical practice, including the disinfection of surfaces, hands and material prior to their usage. The single contamination occurred in an assembly where the spike 30 had no internal valve 71.

The invention claimed is:

1. An adapter configured to couple a withdrawal spike with a multidose vial for maintaining sterility therein, the adapter comprising:

a hollow body defined by an outer wall having a first end and a second end;

a first retaining member at the first end adapted to irreversibly engage at least a portion of the multidose vial such that once the adapter has been engaged with the vial, it is permanently locked in place to prevent removal of the adapter from the vial; and a second retaining member at the second end adapted to irreversibly engage at least a portion of the withdrawal spike, such that the withdrawal spike is locatable in a predetermined position with respect to the multidose vial such that once the spike has been engaged with the adapter, it is permanently locked in place as to prevent removal of the spike from the adapter, wherein the adapter irreversibly couples the withdrawal spike to the multidose vial such that the sterility of the vial contents is maintained after withdrawal of a first and subsequent doses using first and subsequent injection devices.

2. The adapter of claim 1, wherein the first retaining member comprises at least one inwardly extending first projection.

3. The adapter of claim 2, wherein the or each first projection is disposed at a free end of an associated resiliently deflectable tab that is defined by a pair of slots in the outer wall, the slots extending at least partially from the first end towards the second end of the outer wall.

4. The adapter of claim 3, wherein the or each first projection includes a camming surface for engagement by at least a portion of the multidose vial.

5. The adapter of claim 3, wherein the outer wall includes a thinned portion between the ends of the pair of slots at the fixed end of the or each tab to aid tab deflection.

6. The adapter of claim 1, further comprising a flange extending from the second end.

7. The adapter of claim 6, wherein the second retaining member comprises at least one inwardly extending second projection disposed on the outer periphery of the flange.

8. The adapter of claim 7, wherein the or each second projection is disposed at a free end of an associated resiliently deflectable tab that has a fixed end at the outer periphery of the flange.

9. The adapter of claim 8, wherein the or each second projection includes a camming surface for engagement by at least a portion of the withdrawal spike.

10. The adapter of claim 8, wherein the or each tab includes a thinned portion at the fixed end to aid tab deflection.

11. The adapter of claim 6, wherein the flange comprises an annular disc that includes a rim extending about at least a portion of the flange periphery, the flange and rim configured to receive a housing of the withdrawal spike.

12. The adapter of claim 1, further comprising a skirt projecting from the first end of the body.

13. The adapter of claim 12, wherein the skirt is configured to enshroud at least a portion of the multidose vial, with an inner surface of the skirt having a shape that is adapted to match the contours of the relevant portion of the multidose vial.

14. The adapter of claim 1, further comprising at least one gripping surface.

15. The adapter of claim 14, wherein there is a pair of opposed gripping surfaces, each disposed on an outer surface of a boss projecting outwardly from the outer wall of the body.

16. The adapter of claim 1, wherein the adapter comprises a unitary piece.

17. The adapter of claim 16, wherein the adapter comprises a thermoplastic moulding.

18. An assembly comprising:

a multidose vial;

a withdrawal spike adapted to permit multiple sterile withdrawals to be taken from the multidose vial using first and subsequent injection devices; and an adapter configured to couple the withdrawal spike with the multidose vial for maintaining sterility therein during and after withdrawal of a first and subsequent doses therefrom, the adapter comprising:

a hollow body defined by an outer wall having a first end and a second end;

a first retaining member at the first end irreversibly engaging at least a portion of the multidose vial such that once the adapter has been engaged with the vial, it is permanently locked in place to prevent removal of the adapter from the vial; and a second retaining member at the second end irreversibly engaging at least a portion of the withdrawal spike, such that the withdrawal spike is located in a predetermined position with respect to the multidose vial and that once the spike has been engaged with the adapter, it is permanently locked in place as to prevent removal of the spike from the adapter.

19. The assembly of claim 18, wherein the multidose vial comprises: a shell defining an interior chamber having an opening; and a cap hermetically sealing the opening.

20. The assembly of claim 19, wherein the chamber contains multiple doses of a component.

21. The assembly of claim 19, wherein the cap is received in the hollow body of the adapter and is engaged by the first retaining member.

22. The assembly of claim 19, wherein the cap comprises a septum.

23. The assembly of claim 18, wherein the withdrawal spike comprises:

a housing; and a piercing thorn, the thorn protruding centrally and perpendicularly from the housing.

24. The assembly of claim 23, wherein said predetermined position comprises the thorn of the withdrawal spike being inserted through the vial cap by a predetermined distance.

25. The assembly of claim 23, wherein the spike housing is received in the adapter flange and is engaged by the second retaining member.

26. A method of assembling an assembly for administering multiple doses of a component, comprising the steps of:

providing a multidose vial containing the component;

providing a withdrawal spike adapted to permit multiple doses to be taken from the multidose vial;

providing an adapter as defined in claim 1;

fitting the adapter onto the multidose vial; and fitting the withdrawal spike onto the adapter.

27. The method of claim 26, wherein (a) said multidose vial comprises a shell defining an interior chamber having an opening and a cap hermetically sealing the opening, and (b) wherein the first retaining member of the adapter comprises at least one inwardly extending first projection disposed at a free end of an associated resiliently deflectable tab that is defined by a pair of slots in the outer wall, the slots extending at least partially from the first end towards the second end of the outer wall, wherein the first projection includes a camming surface for engagement by at least a portion of the multidose vial, the step of fitting the adapter onto the multidose vial comprising:

engaging the camming surface of the or each first projection with the vial cap;

resiliently deflecting outwardly the associated deflectable tab to a deflected position via a relative axial force between the multidose vial and the adapter; and passing the cap beyond the or each first projection, the or each first projection hence returning from the deflected position to retain the cap within the hollow body.

28. The method of claim 26, (a) wherein said withdrawal spike comprises a housing and a piercing thorn, the thorn protruding centrally and perpendicularly from the housing, and (b) wherein the adapter further comprises a flange extending from the second end, wherein the second retaining member comprises at least one inwardly extending second projection disposed at a free end of an associated resiliently deflectable tab that has a fixed end at the outer periphery of the flange, wherein the or each second projection includes a camming surface for engagement by at least a portion of the withdrawal spike, the step of fitting the withdrawal spike onto the adapter comprising:

engaging the camming surface of the or each second projection with the spike housing;

resiliently deflecting outwardly the associated deflectable tab to a deflected position via a relative axial force between the spike and the adapter; and passing the housing beyond the or each second projection, the or each second projection hence returning from the deflected position to retain the spike housing against the adapter flange.

29. A method of preparing multiple doses of a component comprising the steps of:

assembling the assembly in accordance with claim 26;

inserting an injection device into the withdrawal spike;

withdrawing substantially a sterile dose of component from the multidose vial into the injection device through the spike; and repeating the inserting and withdrawal steps using subsequent injection devices.

30. The method of claim 26, wherein the component comprises a vaccine.

31. The method of claim 30, wherein the vaccine is an influenza vaccine.

32. The assembly of claim 20, wherein the component comprises an influenza vaccine.

* * * * *